United States Patent [19]

Ohman et al.

[11] 4,163,778

[45] Aug. 7, 1979

[54] ASTHMA IMMUNOTHERAPY

[75] Inventors: John L. Ohman, Natick; Francis C. Lowell, Concord, both of Mass.

[73] Assignee: The Foundation for the Study of Asthma and Related Diseases, Boston, Mass.

[21] Appl. No.: 903,025

[22] Filed: May 4, 1978

[51] Int. Cl.$^2$ .................... A61K 35/36; A61K 39/00
[52] U.S. Cl. .................................................. 424/91
[58] Field of Search .......................................... 424/91

[56] References Cited

PUBLICATIONS

Ohman, Kendall, and Lowell, J. Allergy Clin. Immunol., 60(5): 317–323, Nov. 1977, IgE Antibody to Cat Allergens in an Allergic Population.

Ohman, Lowell, Bloch, and Kendall, Clinical Allergy, 6: 419–428, (1976), Allergens of Mammalian Origin V. Properties of Extracts Derived from the Domestic Cat.

Stokes and Turner, Clinical Allergy, 5: 241–254 (1975), Isolation and Characterization of Cat Allergens.

Ohman, Bloch, Kendall, and Lowell, J. Allergy Clin. Immunol., 57: 560–568 (1976), Allergens of Mammalian Origin IV. Evidence for Common Allergens in Cat and Dog Serum.

Ohman, Lowell, and Bloch, J. Immunol., 113: 1668 (1974), Allergens of Mammalian Origin III. Properties of a Major Feline Allergen.

Ohman, Lowell, and Bloch, J. Allergy Clin. Immunol., 52(4): 231–241, Oct. 1973, Allergens of Mammalian Origin: Characterization of Allergen Extracted from Cat Pelts.

Holford-Strevens, Clin. Allergy, 3: 225–234 (1973), Allergenic Activity of Cat and Dog Skin Fractions Obtained by Sephadex Gel Filtration.

Varga and Ceska, Int. Arch. Allergy, 42: 438–453 (1972), Characterization of Allergen Extracts by Polyacrylamide Gel Isoelectrofocusing and Radioimmunosorbent Allergen Assay II. Dog and Cat Allergens.

*Primary Examiner*—Shep K. Rose
*Attorney, Agent, or Firm*—Kenway & Jenney

[57] ABSTRACT

Significant decreases in bronchial sensitivity to cat dander in patients who experience asthmatic symptoms on exposure to cats are achieved by subjecting the patient to immunotherapy employing various dilutions of a cat dander extract containing at least 10% (based on total solids content) cat allergen 1 and, when undiluted, at least 300 micrograms/ml cat allergen 1. Cat allergen 1 is an antigen having a molecular weight between 30,000 and 60,000 daltons. It is identifiable by its ability to form a precipitin line with allergen 1 antiserum. A double blind, rigorously controlled study of the immunotherapy process has demonstrated that significant reductions in bronchial sensitivity may be routinely obtained in asthmatics of this class.

5 Claims, 1 Drawing Figure

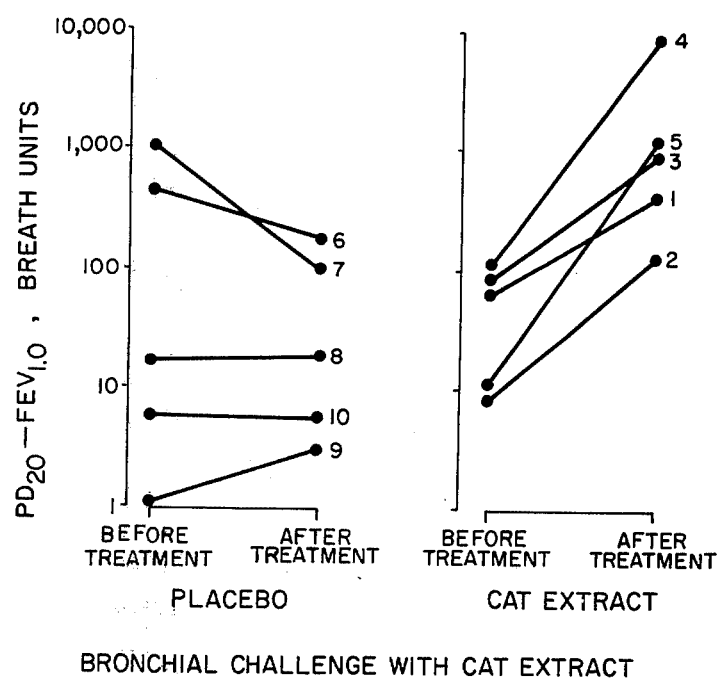
BRONCHIAL CHALLENGE WITH CAT EXTRACT

ASTHMA IMMUNOTHERAPY

BACKGROUND OF THE INVENTION

This invention relates to improvements in immunotherapy techniques for treating extrinsic asthma. More particularly, it relates to an immunotherapy technique for decreasing the bronchial sensitivity to cat dander of individuals suffering from cat-induced asthma.

Extrinsic asthma is an atopic allergic disease induced in susceptible individuals by exposure to certain environmental antigens, called allergens. The disease is characterized by breathing difficulties, wheezing, coughing, and tightness of the chest. Recently, it has been determined that a significant number of extrinsic asthmatics are sensitive to cat dander, and that this form of the disease is particularly severe. It has been reported, for example, that out of 1000 asthmatic children tested by bronchial challenge with dander extracts, 43% were positive. Of 300 consecutive patients with asthma or rhinitis (or both) seen at the Massachusetts General Hospital Allergy Clinic, 82 patients (27%) were aware of symptoms following exposure to cat. Further, it has recently been shown that patients suffering from cat sensitivity are statistically more likely to exhibit the more troublesome asthma symptoms as opposed to those of rhinitis or conjunctivitis.

The treatment of choice for extrinsic asthma is avoidance of the allergen or allergen carrying substance which induces the symptoms. For accidental exposures, or where avoidance is impossible, drugs such as epinephrine, aminophylline, and certain steroids are administered to control the allergic reaction. Asthma as well as other atopic diseases such as rhinitis and conjunctivitis, are sometimes treated with immunotherapy. Immunotherapy refers to the practice of administering extracts of the allergy producing material to an allergic patient in gradually increasing amounts. It can often "desensitize" or "hyposensitize" the patient, i.e., render him less sensitive or less allergic to the allergens used.

Convincing proof that immunotherapy is effective for treating any atopic disease was unavailable until quite recently. Historically, grave doubts have been expressed concerning the utility of the entire approach. However, in the last 20 years, convincing evidence backed up by double-blind studies has demonstrated, at least with respect to immunotherapy directed to the treatment of ragweed induced rhinitis, that this technique can be useful in treating certain patients.

Reports on the effectiveness of attempts to "desensitize" or "hyposensitize" allergic patients to exposure to cat dander have been mixed. For example, Tuft, et al., (Am. J. Med. Sci., V. 253, p. 49, 1967) report that treatment of 18 cat dander sensitive patients (number with asthma unspecified) with alum precipitated pyridine cat dander extracts resulted in significant improvement in the tolerance of most patients to cat exposure. In Annals of Allergy, (Vol. 36, p. 165, March 1976), Tuft, et al. report that hyposensitization with certain unstandardized animal dander extracts can bring about improved tolerance in a sizeable percentage of patients, and compares favorably with that obtained from pollen therapy in hay fever patients. Asthma symptoms were not studied separately. In contrast, Brown, et al., (Annals of Allergy, Vol. 26, p. 305, June 1968) report that attempts at hyposensitization with either unstandardized pyridine or aqueous dander extracts resulted in an insignificant number of improved asthma cases.

The material used for immunotherapy has typically been a crude soluble extract of the allergen bearing agent. For example, in the above noted studies, the extracts employed consisted of the alum precipitated pyridine fraction or the water soluble fraction of cat epithelium. The active allergen content of crude animal epithelial extracts has been unknown and unstandardized, and no controlled studies of immunotherapy in animal dander allergy are available. In fact, the previous reports of immunotherapy directed to animal dander sensitivity are difficult or impossible to evaluate in view of the uncertain qualities of the extracts used. Purified allergens have been used in immunotherapy. See, for example, *A Single Year of Immunotherapy for Ragweed Hay Fever*, Annals of Internal Medicine, Volume 75, No. 5, p. 663, Lichtenstein, et al. However, with purified allergens it is often impossible to know whether all or even most of the relevant allergen content present in the crude material has been included.

Immunotherapy directed to asthma has been reviewed in *Asthma*, K. F. Austen, et al., Academic Press, 1973, p. 211.

SUMMARY OF THE INVENTION

It has now been discovered that aqueous extracts of cat pelts may be treated to exclude much extraneous protein present in the extracts of the prior art, yet to retain the important allergens in concentrated form. The resulting material, if used in an otherwise standard immunotherapy program, leads to clinical results which are unattained in prior art attempts at immunotherapy directed to asthma.

The invention provides a process for reducing the bronchial sensitivity to cat dander of a patient who experiences asthmatic symptoms on exposure to cat. The process comprises the steps of subcutaneously injecting the patient with an extract of cat dander and repeating the injection with extracts of increasing cat allergen content for a sufficient number of times to reduce bronchial sensitivity. The undiluted extract comprises a preparation made from whole cat pelts having a total nondialyzable solids content consisting of at least 10% cat allergen 1, and comprises at least 300 micrograms/ml cat allergen 1. This material has been discovered to be an important asthma allergen, and plays an important but not exclusive role in obtaining the improvement achieved by the process of the invention. Cat allergen 1 is a protein having a molecular weight between 30,000 and 60,000 daltons. It may be identified by its ability to form a precipitin line with purified allergen 1 antiserum produced in accordance with the teachings disclosed herein.

In preferred embodiments of the process of the invention, the total mass of allergen 1 present in the serially administered injections over the course of the typical three month treatment necessary to reach the maintenance dose is between one and five milligrams. It is also preferred to increase the allergen 1 content of the injected extracts during the course of treatment up to the tolerance level of the patient or until an 800 microgram dose is tolerated. Booster injections of the maximum dose at 3–10 week intervals maintain the desensitized state.

One important technique for preparing extracts useful in the process of the invention involves sequential fractionation by ion exchange chromatography and gel filtration. In a first step, a crude aqueous cat pelt extract which is itself capable of inducing asthmatic symptoms is subjected to anionic exchange chromatography on, for example, DE52 cellulose, to isolate a positively charged protein fraction. The allergen rich protein fraction eluted from this column is then subjected to gel filtration to isolate materials of molecular weight less than about 100,000. This may be accomplished, for example, with the aid of certain gels well known in the art and sold commercially under trademarks such as Sephadex G100 and Biogel P100. The material eluted from the second column contains most of the allergenic components present in cat epithelium, and the concentration of irrelevant protein is significantly reduced. Accordingly, the material is well suited for immunotherapy.

It is an object of the invention to provide an effective immunotherapy technique for the treatment of cat induced asthma. Another object is to provide allergen extracts for use in immunotherapy having an improved safety and potency. These and other objects and features of the invention will be apparent to those skilled in the art from the following description of a preferred embodiment and from the drawing wherein the sole FIGURE is a graph illustrating one aspect of the improved results attained by the process of the invention.

DESCRIPTION OF THE PREFERRED EMBODIMENT

The process of the instant invention is specifically directed to individuals diagnosed as having cat induced extrinsic asthma. The patients must have a history of coughing, wheezing, or shortness of breath on exposure to cats. Prior to the initiation of treatment, cat dander sensitivity should be confirmed by a positive skin test. Further confirmation can be obtained if necessary by a positive bronchial challenge response to cat pelt extract.

As with conventional immunotherapy techniques, treatment is initiated by subcutaneously injecting the patient with small amounts of diluted extract given, for example, at once or twice weekly intervals. The dose of extract is doubled as tolerated until the patient's maximum tolerated dose is reached or the maximum quantity of extract recommended (as set forth below) is administered. The highest dose is repeated at 3-10 week intervals for maintenance. The duration of treatment before maximum or maintenance doses are reached will be 3 to 4 months and the total number of injections will be between about 15 and 35. Patients should be required to remain on the premises for one-half hour after each injection so systemic allergic reactions, if any, can be treated. Following a systemic reaction, the patient's next injection dose should be reduced, e.g., four fold, and the treatment cautiously resumed.

The foregoing procedure differs from conventional immunotherapy procedures primarily with respect to the nature of the extract used. In accordance with the invention, the extract contains at least 300 micrograms/ml, and on the basis of solids content, at least 10% by weight of a protein having a molecular weight between 30,000 and 60,000 daltons of a nature hereinafter described and referred to as "cat allergen 1". A technique for isolating this allergen from cat pelts is disclosed in the Journal of Immunology, Vol. 113, p. 1668 (1974) in a paper entitled *Allergens of Mammalian Origin III Properties of a Major Feline Allergen*, by Ohman, et al. The measurement of allergen 1 content in commercial cat epithelial extracts has been shown to be useful as an allergen extract standardization technique. See, Clinical Allergy, Volume 6, page 419, (1976), *Allergens of Mammalian Origin. V*, Ohman, et al. While the presence of at least 10% and 300 micrograms/ml allergen 1 in the extracts used in the immunotherapy process of the invention both sets the process apart from prior art techniques and is necessary if the improved results are to be achieved, the use of "pure" allergen 1 is not recommended. This is because, among members of the class of individuals sensitive to cats, different patients sometimes react to different allergens in cat dander, and patients may experience asthmatic symptoms on exposure to several cat dander allergens.

Cat allergen 1 is an exceedingly complex protein, and as such, its chemical structure has not been elucidated. However, a determination of the presence and concentration of cat allergen 1 in a given cat pelt extract can readily be made using purified cat allergen 1 antiserum produced in accordance with the following procedure.

Preparation of Allergen 1 Antiserum

Fresh, unshaved cat pelts are washed with water and lyophilized, (Model USM-15, the Virtis Company, Inc. Gardiner, New York) for 72 hours. The lyophilized extracted pelts are then defatted in ether, throughly dried, and extracted with water (1:10 W/V) at room temperature, for 6 hours and overnight at 5° C. After adjusting the pH to 7.5 with 0.1 N NaOH, the water soluble extract is separated from pieces of pelt by pressing through dacron gauze. Particulate matter and bacteria are removed by passing the extract through filters of successively smaller pore size (final pore size 0.22 micron). Aliquots of crude extract are then lyophilized and stored under sterile conditions at 5° C. The lyophilized protein from 100 ml of the crude pelt extract is then reconstituted in three milliliters of water and dialyzed against 0.05 M NaCl in phosphate buffer (0.01 M, pH=7.5) for 48 hours at 5° C. to remove low molecular weight, inactive materials. Next, the reconstituted 3 milliliter portion of extract is subjected to anionic exchange chromatography to isolate positively charged protein containing allergen from extraneous protein. The extract is accordingly applied to a 2×30 cm chromatographic column packed with DE52 cellulose micogranules (Reeve Angel, Clifton, N.J.) and equilibrated against the above solution. Following elution of a first peak of protein, a second protein fraction containing allergen is eluted by increasing the concentration of the NaCl to 0.25 M. The material in this second fraction contains most of the allergenic activity, and after dialysis against 0.05 M ammonium carbonate and concentration by lyophilization, is ready for further purification.

A Sephadex G100 column (2×100 cm) is next equilibrated with 0.15 M saline (buffered to pH 8.0). Two milliliters of the sample are dialyzed against this buffer, and the sample is applied to the columns at 4° C. to separate protein fractions of differing molecular weight. Two protein peaks are obtained. The portion of the eluate constituting the second peak including the entire descending limb is pooled and concentrated by lyophilization.

Substantially all allergenic activity present in the original crude extract residues in this fraction, and at least 10% of the protein mass of this fraction comprises allergen 1. Typically, allergen 1 is present in substantially greater percentages, and the fraction exhibits a 50 fold increase in specific activity over the crude preparation. Advantageously, other as yet unidentified allergens capable of inducing asthmatic symptoms in a sensitized patient are also present in this fraction. This material accordingly has a potency, safety, and purity which make it well suited for use in the immunotherapy technique of the invention.

The fraction prepared as disclosed above is next subjected to polyacrylamide disc gel electrophoresis using glass tubes measuring 6 by 100 millimeters. The separator gel contains 7% acrylamide. A current of 4 mA per tube is applied until bromphenol blue (use as an indicator) has migrated 50 millimeters into the small pore gel. The gel columns are then removed from the glass tubes and one is stained with 1% amido-black in 7% acetic acid. Excess stain is removed by leaching in 7% acetic acid. Fractions of unstained gel columns are prepared by embedding the columns in 1% agar immediately after electrophoresis and slicing the gel into 5 millimeter cylinders. The cylinders are then homogenized and fractions are eluted with 1.0 ml aliquots of 0.15 M NaCl at 20° C. for 6 hours and overnight at 5° C. Five distinct protein bands are seen in the stained columns. Allergenic activity is largely recovered from unstained columns in an area corresponding to the first two bands. The second band (band B) comprises cat allergen 1 plus cat albumin as a contaminant.

Laboratory animals are immunized with 1 milligram of band B protein emulsified in Freund's complete adjuvant. After 30 days, antiserum is collected which contains antibody to band B and to cat albumin. This material produces a precipitin line with the material of band B obtained as described above by electrophoesis in 7% acrylamide gel, and in addition, a distinct precipitin line with a component present in both band B and purified cat albumin. In order to remove antibody directed against albumin, the antiserum is passed through an immunoabsorbent column comprising cat albumin conjugated to a sepharose sugar (sepharose 4B). Following absorption, the antiserum produces a single precipitin line against band B.

Allergen 1 antiserum produced as disclosed above may be used to determine the allergen 1 content of any cat epithelial extract in accordance with the procedure set forth in *Allergens of Mammalian Origin. V,* Clinical Allergy, Vol. 6, p. 419 (1976). Briefly, the technique for determining allergen 1 content involves radial immunodiffusion in agarose gel. Four milliliters of antiserum are mixed with 20 milliliters of 1% agarose in phosphate buffered saline at 56° C. and poured onto lantern slides. A series of wells measuring 3 millimeters in diameter are cut into the agarose layer after it has hardened and 20 microliters of antigen containing solution are placed in the wells. After 48 hours, the diameter of the precipitin ring is measured. Dilutions of standard antigen solution are included on each slide, and a linear relationship is observed between the log of the diameter of the precipitin ring and the log of the concentration of antigen.

Using this technique, it has been determined that commercially available cat epithelial extracts contain between one and 25 micrograms per milliliter cat allergen 1. Expressed as a percentage of total solids, cat allergen 1 content ranges between about 0.25% and 6.2%. In contrast, the material used in the process of the instant invention contains at least 300 micrograms/ml cat allergen 1 and comprises at least 10% cat allergen 1. A double-blind test demonstrating the improved results obtainable with the process of the invention and disclosing details of one treatment protocol is set forth below.

Preparation of Extract

A single pool of crude cat pelt extract was prepared from lyophilized cat pelts as described above. The pool was lyophilized and divided into aliquots which were reconstituted immediately prior to use. Cat allergen 1 content of the extracts was measured by radial immunodiffusion.

For immunotherapy, a solution containing 15.2 mg/ml total solids and 1.6 mg/ml cat allergen 1 (10.5 percent), and a placebo solution containing 0.55 mg/ml histimine phosphate were prepared. Both the active and the placebo solutions were colored to be identical in appearance. Three serial 10 fold dilutions of the active and placebo solutions were made.

For skin testing and bronchial inhalation challenge, a solution containing 0.19 mg/ml total solids and 0.02 mg/ml cat allergen 1 was prepared. Six serial 10 fold dilutions of this solution were made.

Patient Selection

Patients were selected who were in good health and without perennial asthma. All gave a history of coughing, wheezing, or shortness of breath on exposure to cats. All gave a positive skin test and positive bronchial challenge response to cat pelt extract. Also, each patient's one second forced expiration volume ($FEV_{1.0}$), measured with a kymographic tracing obtained on a 6 liter recording spirometer, was determined to be at least 80% of the predicted value as a condition precedent to participation in the double blind test.

Skin Testing

Prick tests were performed as described in *Allergens of Mammalian Origin,* Ohman, et al., J. Allergy. Clin. Immunol. Vol. 52 p. 231, (1973). The average diameter of the flare was noted after 15 minutes. Reactions of 5 millimeters or greater were regarded as significant and were recorded.

Bronchial Inhalation Challange with Antigen and Histamine

Solutions were aerosolized with a DeVilbiss No. 40 nebulizer connected to a compressed air source with a flow of 10 liters per minute. Patients were instructed to inhale the aerosol from residual volume to inspiratory capacity and then hold their breath for two seconds. The $FEV_{1.0}$ measurements were made 10 minutes following inhalation of cat pelt extract and three minutes following inhalations of histamine. The initial dilution of cat pelt extract used for inhalation challenge was determined by prick test end point titration: the most dilute solution that gave a positive prick test response was determined, and then a 10 fold more dilute solution was used. For the histamine inhalation challenge, concentrations of 0.01, 0.1, 1.0, 10, and 20 mg/ml were used.

Five inhalations of successively more concentrated solutions of cat pelt extract or histamine were tested until the $FEV_{1.0}$ dropped 20% or more compared with the base-line values. A "breath unit" was defined as one inhalation of a 1:100 dilution of cat pelt extract, and one inhalation of a 1.0 mg/ml solution of histamine. The provocation dose in breath units that resulted in a 20% drop in $FEV_{1.0}$ was determined for each patient, both before and after therapy.

Protocol for Double-Blind Study

Patients who met the criteria noted above were randomly assigned to active treatment or placebo groups. Each patient's treatment mixture was coded prior to the study and the code was not broken until its conclusion. Immunotherapy was started by an initial subcutaneous injection of 0.1 ml of a 1:1000 dilution of the extract given at twice weekly intervals. The dose of extract was doubled as tolerated until the patient's maximum tolerated dose was reached or 0.5 ml of the undiluted extract was given. The highest dose was repeated 4 to 6 times for each patient.

At the conclusion of the study, and one week after the last injection of the cat pelt extract, the prick test end point titrations and the bronchial inhalation challenges with cat pelt extract and histamine were repeated. Because of the probability that systemic reactions to the immunotherapy would partially unblind the study, an investigator not involved in the immunotherapy was assigned to conduct the final inhalation challenges. Patients were instructed not to discuss their immunotherapy with the investigator.

Results

The results on 10 representative patients found suitable for entrance into the study are set forth in tables 1 and 2 below.

Table 1

Patient Characteristics

| Patient (a active p = placebo) | Age, Years | Sex | $FEV_{1.0}$ (% of predicted) | Total Solid mg | Cat Allergen 1, mg |
|---|---|---|---|---|---|
| 1a | 24 | F | 100% | 44.8 | 4.7 |
| 2a | 28 | F | 87% | 41.7 | 4.4 |
| 3a | 28 | F | 88% | 44.0 | 4.6 |
| 4a | 33 | F | 103% | 17.3 | 1.8 |
| 5a | 20 | F | 100% | 16.4 | 1.7 |
| 6p | 29 | M | 110% | — | — |
| 7p | 43 | F | 91% | — | — |
| 8P | 21 | F | 80% | — | — |
| 9p | 27 | F | 84% | — | — |
| 10p | 30 | F | 83% | — | — |

Table 2

Skin Test Reactions

| | Highest dilution of cat pelt extract giving a positive prick test reaction | |
|---|---|---|
| Patient | Before Treatment | After Treatment |
| 1a | 1:100 | undiluted |
| 2a | 1:10 | negative* |
| 3a | 1:10 | negative* |
| 4a | 1:10 | negative* |
| 5a | 1:100 | undiluted |
| 6p | undiluted | undiluted |
| 7p | 1:100 | 1:10 |
| 8p | undiluted | 1:10 |
| 9p | 1:1000 | 1:10 |
| 10p | 1:10 | 1:100 |

*negative prick test reaction to undiluted extract

As illustrated in Table 1, the cumulative cat allergen 1 dose over the course of the three to four month period of the study ranged between 1.7 and 4.7 milligrams. Table 2 summarizes the results of prick test end point titrations before and after treatment. As noted, all five patients who receive the active treatment showed a reduction in level of skin reactivity. Of the patients receiving the placebo, two showed a reduction in skin reactivity, two showed an increase in skin reactivity, and one patient remained the same.

Before treatment, the mean provocation dose in breath units which resulted in a 20% drop in $FEV_{1.0}$ ($PD_{20}$-$FEV_1$) in the placebo and active treatment groups was not significantly different. In the placebo group, there was no significant change in mean $PD_{20}$-$FEV_{1.0}$ with treatment. In the active treatment group there was a significant rise in this variable (See drawing). All five patients receiving the active treatment showed a marked decrease in bronchial sensitivity to cat pelt extract. In contrast, there was no significant change in the mean $PD_{20}$-$FEV_{1.0}$ with treatment in either the placebo or active treatment groups to challange with histamine. Accordingly, the significant decrease in bronchial sensitivity to cat pelt extract in the active treatment group could not be explained by a decrease in nonspecific bronchial activity (as measured by bronchial sensitivity to histamine). The rigid nature of the foregoing double blind protocol and careful patient selection permit the accumulation of truly significant results from a small number of patients, and as is obvious from the foregoing data, the results were undeniably positive. The success of the treatment is believed to be due to the presence and concentration of the allergens in the extracts used, and particularly to the high concentration of cat allergen 1. The low concentration of cat allergen 1 in commercial cat epithelial extracts would make it difficult or impossible to achieve cumulative doses similar to those used here unless very large volumes of extract were administered. As noted above, the cat allergen 1 content in 1:10 W/V commercial cat epithelial extracts range from 1.0 to 25 micrograms/ml. Thus, about 68 milliliters of the commercial extract containing the greatest concentration of cat allergen 1 would be required to equal the minimum cumulative dose used in the foregoing study. Further, about 32 ml of the commercial extract containing the highest concentration of allergen 1 would be required to achieve an allergen content corresponding to the highest single dose (0.5 ml, 800 micrograms) used in the process of the invention.

The invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A process for reducing the bronchial sensitivity to cat dander exposure of a patient who experiences asthmatic symptoms on exposure to cat, said process comprising the steps of subcutaneously injecting the patient with an extract of cat dander and repeating the injection with extracts of increasing cat allergen content for a sufficient number of times to reduce bronchial sensitivity, wherein the improvement comprises
   employing as an extract a preparation made from cat pelts having a total nondialyzable solids content comprising at least 10% by weight cat allergen 1, and containing at least 300 micrograms per milliliter of cat allergen 1,
   said cat allergen 1 consisting essentially of a protein having a molecular weight between 30,000 and 60,000 daltons and being identifiable by its ability to form a precipitin line with allergen 1 antiserum purified by absorption with cat albumin.

2. The process of claim 1 wherein the cat pelt extract contains other allergens capable of inducing asthmatic symptoms.

3. The process of claim 1 wherein the cat allergen 1 content of the injected extracts is increased up to the tolerance level of the patient over the course of treatment.

4. The process of claim 1 wherein the total mass of allergen 1 administered over the course of treatment is between one and five milligrams.

5. The process of claim 1 wherein the cat pelt extract is prepared by:
   A. subjecting a crude aqueous cat pelt extract capable of inducing asthmatic symptoms to anionic exchange chromatography to isolate a positively charged allergenically active protein fraction; and
   B. subjecting the fraction isolated in step A to gel filtration to isolate protein in the molecular weight range of 10,000 to 100,000 daltons, the protein collected comprising at least ten percent cat allergen 1.

* * * * *